United States Patent
Traber et al.

(10) Patent No.: US 6,788,986 B1
(45) Date of Patent: Sep. 7, 2004

(54) METHOD FOR PRODUCING AN INDIVIDUALLY MADE, IMPLANT-SUPPORTED TOOTH REPLACEMENT

(75) Inventors: Tony Traber, Allschwil (CH); Heinrich F. Kappert, Gundelfingen (DE); Rainer Glaeser, Freiburg i. Breisgau (DE)

(73) Assignee: DCS Forschungs & Entwicklungs AG, Allschwil (CH)

( * ) Notice: Subject to any disclaimer, the term of this patent is extended or adjusted under 35 U.S.C. 154(b) by 22 days.

(21) Appl. No.: 09/595,609

(22) Filed: Jun. 16, 2000

(30) Foreign Application Priority Data

Jun. 21, 1999 (CH) .............................................. 1151/99

(51) Int. Cl.[7] .............................................. G06F 19/00
(52) U.S. Cl. ..................................... 700/98; 433/201.1
(58) Field of Search .......................... 700/98, 117, 118, 700/119, 163; 433/172–176, 201.1, 214, 215

(56) References Cited

U.S. PATENT DOCUMENTS

| 5,184,306 A | | 2/1993 | Erdman et al. ............. 700/163 |
| 5,347,454 A | | 9/1994 | Mushabac ................... 433/214 |
| 5,564,921 A | * | 10/1996 | Marlin ........................ 433/172 |
| 5,816,810 A | | 10/1998 | Antonson et al. ........... 433/173 |
| 5,857,853 A | | 1/1999 | van Nifterick et al. ..... 433/213 |
| 5,873,721 A | * | 2/1999 | Willoughby ................. 433/173 |
| 5,880,962 A | * | 3/1999 | Andersson et al. ........... 700/98 |
| 6,049,743 A | * | 4/2000 | Baba ........................... 433/172 |
| 6,287,121 B1 | * | 9/2001 | Guiot et al. ................. 433/218 |

FOREIGN PATENT DOCUMENTS

| EP | 0599578 A2 | 6/1994 |
| JP | 52-80391 | 10/1993 |
| JP | 6-154252 A | 3/1994 |
| WO | WO 98 44864 A | 10/1998 |

* cited by examiner

*Primary Examiner*—Leo Picard
*Assistant Examiner*—Ryan Jarrett
(74) *Attorney, Agent, or Firm*—Townsend and Townsend and Crew LLP; Guy W. Chambers

(57) ABSTRACT

A method for producing an implantable tooth replacement (10) in which tooth-like superstructure material (21) can be mounted in a common insertion direction. The method of the present invention preferably begins with a manipulation implant (42) being attached to a working model (4) of a jaw area (30), which is to be provided with the tooth replacement (10). An abutment (18) is made for each implant (12), which is intended to be positioned on the implant (12) by means of a positioning device (15) and to be fastened by means of a fastening element. A super-structure (21) is made on the working model (40) which fits on the abutment (18) and is intended to be pushed later on the at least one abutment (18) in the jaw area (30).

10 Claims, 8 Drawing Sheets

METHOD FOR PRODUCING AN INDIVIDUALLY MADE, IMPLANT-SUPPORTED TOOTH REPLACEMENT

FIELD OF THE INVENTION

The invention relates to a method for producing an individually made, implant-supported tooth replacement, in particular from any arbitrary, also biocompatible, materials, and more particularly with the aid of CAD-CAM technology. The invention further relates to a method for producing a tooth replacement element, which is intended to be positioned and fastened on at least one implant, or at least one tooth stub.

BACKGROUND OF THE INVENTION

Within the scope of the present invention, the term "tooth replacement" is understood to be a structure which complements or replaces not only the visible portion of a tooth or a group of teeth, but also its root, and which therefore constitutes a complete replacement of one or several teeth of a patient. In the finished state, this tooth replacement consists of several components, which are interlocked or fastened on each other. Thus, within the scope of the present invention, the term "tooth replacement element" is understood to be a structure which is supported on an implant or a tooth stub, and which essentially projects past the jawbone and the gums. A tooth replacement element can in particular constitute a component of an implant-supported tooth replacement.

The first component of the tooth replacement is an implant, which is inserted into the jawbone of the patient and is then also called an implant insertion. The further components of the tooth replacement will be later built on this implant insertion. The implant insertion generally constitutes the basis for a tooth replacement replacing one or several teeth. A tooth replacement intended to replace one tooth is supported on a single implant, and a tooth replacement intended to replace several adjoining teeth is generally supported on at least two implants. The implants are intended to be implanted, or respectively inserted, by the dentist into the jawbone of a patient, and they are provided by the dentist ready to use and sterilized. The implants can be essentially designed to be cylindrical or tapering and are in the form of screws or pins. On its crown end, each implant has a positioning element. In the installed state of the tooth replacement, the implants are not visible on the patient, or only to a limited degree.

The second component of the tooth replacement is constituted by a connecting element, which in technical terms is called an abutment. One abutment is fastened on each implant. In the installed state of the tooth replacement the abutments are not visible in the patient, or only to a limited degree. They are used to connect the implants with the further components of the tooth replacement. Each abutment has a second positioning element on its proximal end which, together with the first positioning element arranged on the associated implant, forms a positioning device providing protection against rotation.

The third component of the tooth replacement is constituted by connecting elements, generally screws, for the mutual fastening of the implant and the abutment. These connecting elements are also not visible in the patient in the installed state of the tooth replacement. The mutual connection of the implant to the abutment is generally reversible.

The fourth component of the tooth replacement is called a framework, bridge frame or cap. It is secured against vertical displacement, or respectively fastened, on one or several abutments, generally with the aid of a suitable cement or adhesive, or by means of a horizontal or vertical screw connection. The individual cap can be used for replacing one tooth and can be mounted on one abutment. However, a structure made of several caps in connection with an intermediate member, called a portic, can also be intended as the bearing element for an implant bridge for replacing several teeth, and can be mounted on several abutments. Although caps are not, or only slightly, visible after the tooth replacement has been installed in the patient, their nature can have a certain influence on the esthetic aspect of the tooth replacement, which will be explained further down below.

The fifth component of the tooth replacement is constituted by a facing, which encloses the framework, or respectively the bridge frame, or respectively the cap. The facing is the only component of the tooth replacement which is visible in the installed state of the tooth replacement of the patient. The facing is intended to replace the visible area of the tooth. The framework, or respectively the bridge frame, or respectively the cap, on the one hand, and the facing on the other, are irreversibly connected with each other.

It is also possible to use a so-called full crown in place of the framework, or respectively the bridge frame, or respectively the cap, as well as the facing which, as just described, constitute the fourth and fifth component of the tooth replacement. In this case the tooth replacement comprises only four components, namely the implant, the abutment, the connecting elements and the full crown.

The framework and the facing together, or the full crown by itself, form a unit which will also be called a supra-structure within the scope of the present description. The supra-structure is fastened reversibly or irreversibly on the abutment. Reversibly fastened supra-structures can be removed from the abutment, if required.

In regard to functionality, shape and appearance, the tooth replacement should be as similar as possible to the natural tooth, or respectively the natural teeth, to be replaced, of the patient.

As already mentioned, within the scope of the present description the term tooth replacement should be understood to be a structure intended to be fastened directly or indirectly on implants or tooth stubs. On the one hand, the term tooth replacement includes abutments which are fastened on implants, frameworks which are fastened on abutments, and facings which are attached to the frameworks, furthermore also abutments which also constitute frameworks, and integral parts which include all components of a tooth replacement, with the exception of the implant itself. On the other hand, elements which can be fastened on prepared teeth, such as crown- or bridge-like elements, also fall under the term tooth replacement.

The production of implantable tooth replacements can take place in various ways, and the tooth replacement being made can also be embodied differently, as described above. In general, the planning and production of a tooth replacement comprises several method steps described in what follows, which are partially performed by a dentist and partially by a dental technician.

The area of responsibility of the dentist starts with the preparation of a negative impression, which is also called a jaw impression. The making of a negative impression, or respectively a jaw impression, is a method step wherein a measurement is taken of the patient, but which does not leave a trace on the patient, or respectively does not result in changes. Thereafter, a working model is made by the dental technician on the basis of the jaw impression. The working model represents the conditions in the jaw of the patient in which the tooth replacement is to be integrated. The dentist provides information regarding the number of implants, as well as other information, as required. Furthermore, the dentist inserts the implants. Another negative impression is taken after the insertion of the implants, which provides more accurate information to the dental technician, which will be described further down below. Following the prescribed required healing phase following the insertion of the implants in the jaw of the patient, the dentist lays the implants, or respectively their outer areas, open. The optimum position of the implants is of decisive importance for the shape of the further components in respect to occlusion, function and appearance. Unfortunately it is not always possible in the course of inserting the implants in the jaw of the patient to arrange them optimally in respect to the ideal expectation regarding occlusion, function and appearance. The result of this is that in respect to occlusion, function and appearance the tooth replacement can often not be optimally placed in the mouth of the patient. After some time, during which the implants grow in, the dentist finally attaches the remaining components of the tooth replacement on the implants.

As mentioned above, the dental technician begins with the production of a working model, which is made on the basis of the negative impression, or respectively the jaw impression provided by the dentist. The working model is always used in the further process. The essential work steps in producing the tooth replacement be performed on the working model.

Depending on the tooth replacement to be made, the dental technician inserts one or several manipulation implants, which are also called an analogous cast, in the working model. The manipulation implants are not a part of the tooth replacement to be made, they are merely aids for producing the tooth replacement. The analogous cast forms the basis for making the remaining components of the tooth replacement. The position of the analogous cast is determined by the jaw impression with the implants provided by the dentist. The precise representation of the positions of the implants is of decisive importance for the further production of the tooth replacement.

An abutment is attached to each model implant arranged on the working model. There are several possibilities for procuring suitable abutments. Premanufactured abutments can be used, which is a more cost-effective and less time-consuming possibility for producing individual abutments. Individual abutments can be produced by means of a molding process which, however, has several disadvantages. It is difficult in connection with bridge and similar constructions in particular to produce an accurate shape as well as a stress-free structure. Furthermore, there is the danger of temperature-related changes of the material during molding. Individual abutments can be individually produced as individual parts, wherein they are individually made either from a blank or a plate. Finally, ready-made abutments, which are then finished or individualized, for which purpose they are fastened on a plate-shaped holding device, can also be used for the production of individual abutments. In any case, the production of individualized connecting bodies is expensive.

A large amount of time is required when producing bridges which are supported by implants, namely in connection with pushing the supra-structures on the implants and abutments. While the insertion process in the course of producing a crown-like tooth replacement, which extends only over the area of one tooth, does not have too many problems, it is considerably more problematical when providing a bridge-like tooth replacement extending over the area of several teeth, since in this case the supra-structure is indirectly supported on several implants and directly on several abutments. The implants, or respectively their longitudinal axes, are generally not arranged parallel, but diverging, and therefore require corresponding divergent insertion directions. But a supra-structure produced in one piece in the form of a bridge can only be pushed in in a single insertion direction, this means that the insertion direction on several implants, or respectively abutments, must be parallel, which at present is only possible under difficult conditions. With large divergences the placement becomes impossible, or becomes only possible when manual finishing work has been performed, which requires a large outlay. With lesser divergences it is still possible to perform the placement in the mouth of the patient, however, only by the generation of large stresses of the implants and/or the abutments and/or the supra-structure.

It is extraordinarily difficult at present to obtain a stress-free structure with unchanged material properties of the tooth replacement with the conventional methods.

OBJECT AND SUMMARY OF THE INVENTION

It is therefore the object of the invention to propose an improved method for producing an individual, implant-supported tooth replacement, and to propose an improved method for producing an individual tooth replacement element, i.e. an individual tooth replacement element made of one or several elements, which can be mounted on at least one implant or at least one tooth stub.

For producing the tooth replacement, a negative impression, or respectively a negative impression of the jaw or jaw area in which the tooth replacement to be produced will later be placed, is made by the dentist, the same as in connection with conventional methods, in order to obtain information regarding the position of the base, or respectively the implant or implants. A working model is made by the dental technician on the basis of this negative impression. A manipulation implant arrangement, whose position corresponds to the implants in the mouth of the patient, is subsequently attached. The manipulation implant arrangement can consist of one or several manipulation implants corresponding to the number of actual implants. The manipulation implants do not or hardly project out of the working model, the same as the implants do not or hardly project out of the corresponding jaw area of the patient. Therefore an auxiliary element is provisionally attached to each manipulation implant. These auxiliary elements project out of the working model and constitute auxiliary elements, or respectively measuring elements, because they reproduce the insertion depth, the direction of the longitudinal axes and the angular position of the manipulation implants in the working model, and therefore also the implant depth, the axial direction of the implants and the angular position of the implants in the mouth of the patient. With the aid of these auxiliary elements or measuring elements it is subsequently possible to acquire data regarding the geometry of the working model, from which it is possible to draw conclusions regarding the exact position of the implants in the jaw area of the patient. Further data can be determined from the data once acquired, which are needed for the fully automated production, as well as for the determination of the insertion direction of the further components of the individual tooth replacement. In particular, it is possible to produce the components of a tooth replacement containing several implants in such a way, that placement can take place in a single insertion direction, which is also called a parallel insertion direction. In this way a degree of precision, which up to now had not been attained, is achieved in every respect.

The production in accordance with the invention of a tooth replacement element by the novel method is essentially the same as the production of a tooth replacement, with the exception of the method steps which solely relate to the implants, since tooth replacement elements are supported either on existing tooth stubs or on implants which are considered to exist.

Further details and advantages of the invention will be described in what follows by means of exemplary embodiments and while making reference to the drawings.

DETAILED DESCRIPTION OF THE PREFERRED EMBODIMENTS

Figure 1:
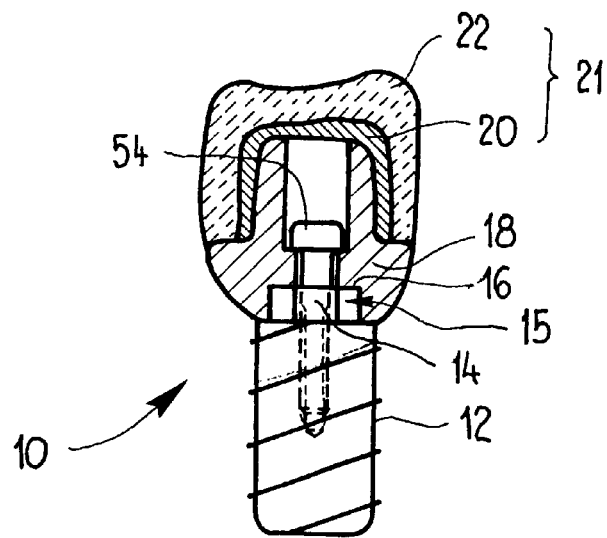
FIG. 1 shows a tooth replacement in accordance with the invention in a sectional view containing the longitudinal axis of the tooth replacement.
Figure 7B:
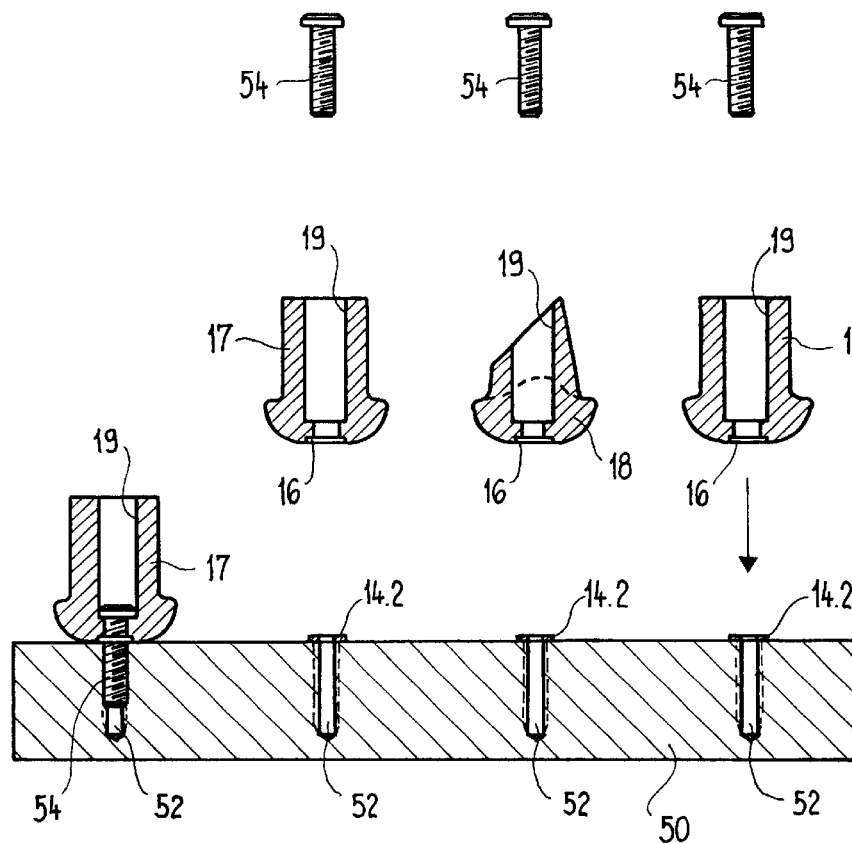
FIG. 7A is a view from above on a plate for receiving abutment blanks, on which several abutments can be fixed in place while being processed, FIG. 7B, in a sectional view perpendicularly in respect to the main plane of the plate, shows the plate represented in FIG. 7A with an abutment blank fastened on the plate, and with three abutments which have not been fixed in place, as well as the associated fastening screws.
Figure 7A:
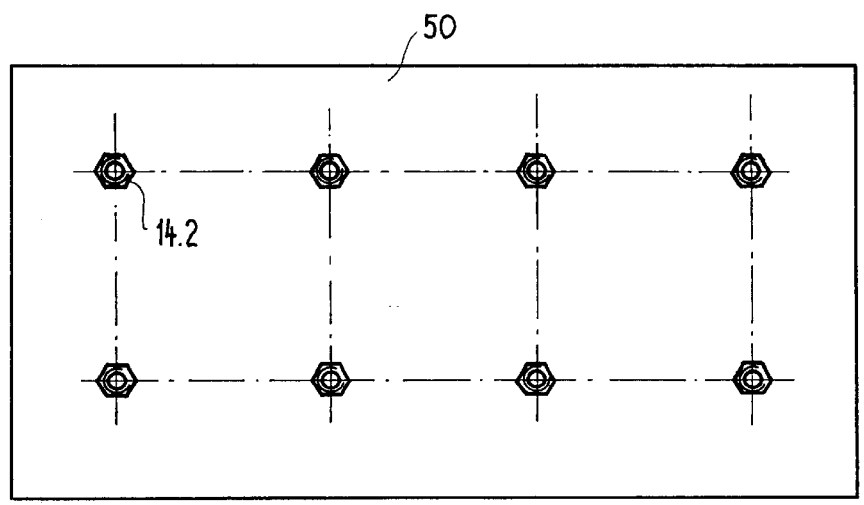

A complete individual tooth replacement 10 is represented in FIG. 1. The individual tooth replacement comprises an implant 12, which constitutes the basis for further components of the individual tooth replacement 10. Here, the implant 12 is designed as a screw, but it can also be designed as a tube or a pin. The implant 12 is designed to be fastened in the jawbone of the patient as a replacement for the root of the tooth. On its end at the top in FIG. 1, the implant has a first positioning element 14 of a positioning device 15. A second positioning element 16, designed complementary to the first one represented, of the same positioning device 15 is arranged on an abutment 18 and is represented in FIGS. 7A, 7B. A through-bore 19, also called a mounting channel, is also visible in FIG. 7B, which is provided for receiving a fastening element, such as a screw 54, by means of which the abutment 18 is fastened on the implant 12. An appropriately suitable implant 12 is selected from a number of different mass produced implants and is implanted by the dentist without further processing in the jawbone of the patient. In accordance with FIG. 1, a framework 20, which is also called a cap, has been built up on the abutment 18. Different materials and production techniques, which will be described further down below, can be used for the framework 20. A facing 22 is fastened on the framework 20 which, together with the framework 20, constitutes a unit, called supra-structure 21, or mesiostructure 21 within the scope of the present description, of the individual tooth replacement 10. Essentially, the facing 22 constitutes the replacement for the visible portion of the tooth enamel. FIG. 1 is only used to describe the components of which the individual tooth replacement 10 consists, which is installed in the mouth of the patient, but not for describing the actions in the course of constructing, or respectively mounting, the individual tooth replacement 10.

Figure 2:
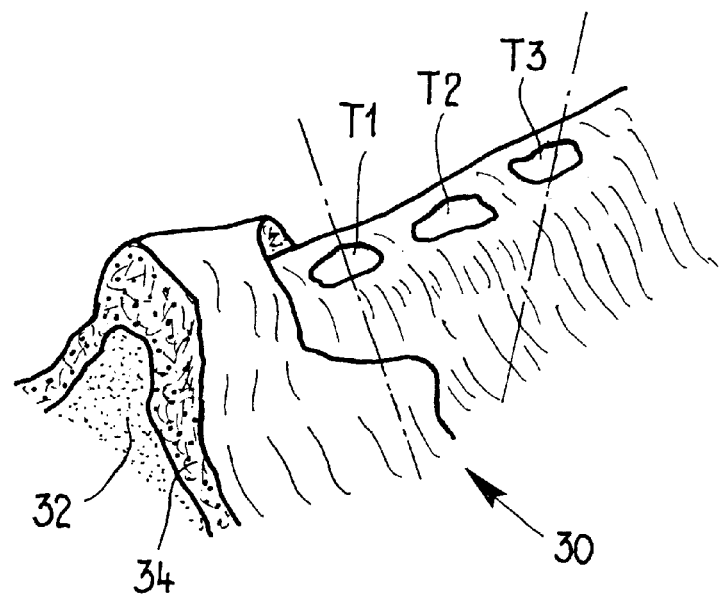
FIG. 2 is a diagram of the jaw area of a patient prior to the insertion of the implants.

FIG. 2 represents portions of a jaw area 30 with a jawbone 32 and gums 34 of a patient which is to be provided with a bridge-like individual tooth replacement 10, namely at positions T1, T2, T3, where originally three adjoining teeth had been. A jaw impression, not represented, in the form of a negative cast, or respectively negative impression, is made by the dentist in this jaw area. The dentist furthermore will implant, or respectively insert, an implant 12, not represented in FIG. 2, respectively at the positions T1 and T3, and will fasten the further components of the individual tooth replacement 10, which are produced by the dental technician, on these two implants 12 as soon as they have been integrated into the bone. In addition, the dentist provides information regarding the position of the two implants 12 and the desired embodiment of the further components of the individual tooth replacement 10.

Figure 3:
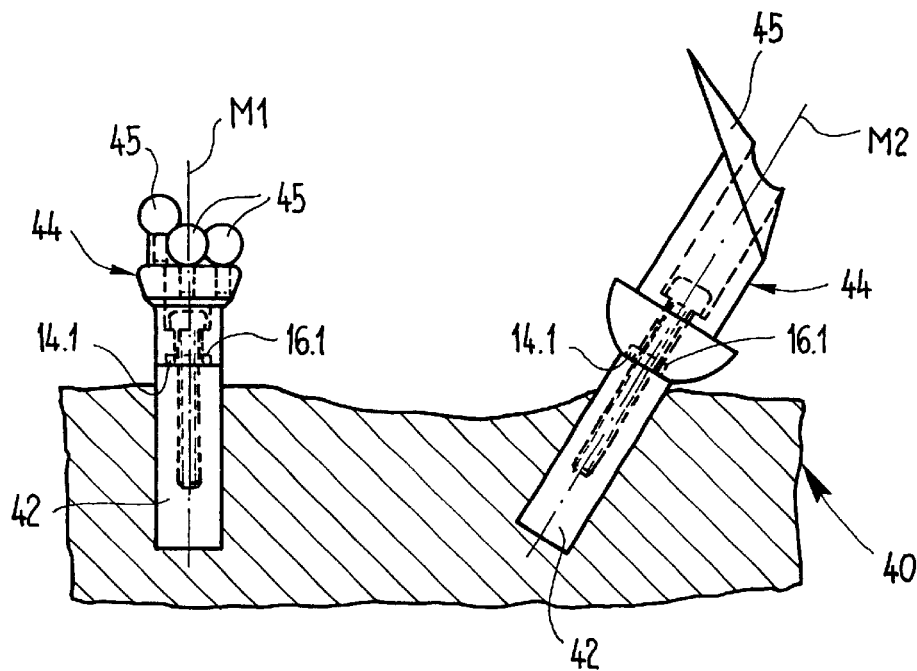
FIG. 3 shows portions of a working model of the jaw area represented in FIG. 2, having two divergently placed implants and one auxiliary element per implant, in a simplified sectional view.

One or several working models, in particular a working model 40 shown in part in FIG. 3, will be produced by the dental technician on the basis of the negative impression, or respectively jaw impression, made by the dentist. The working model 40 is used by the dental technician as the basis for making the individual, bridge-like tooth replacement 10, which is intended to replace the three teeth originally existing at T1, T2 and T3. As already mentioned, the bridge-like individual tooth replacement 10 has the two implants 12 as its basis. Now two manipulation implants 42 are fastened on the working model 40, namely at position, or respectively with longitudinal axes M1, or respectively M2, which correspond as exactly as possible to the positions, or respectively main directions T1 and T3 of two of the three teeth to be replaced.

It is alternatively also possible to obtain the working model on the basis of an impression of the jaw area containing the implants 12, wherein generally no manipulation implants 42 are needed.

The production phase of the individual tooth replacement 10 is represented in FIG. 3, in which a provisionally associated auxiliary element, or respectively measuring element 44, is arranged on each one of the manipulation implants 42. These auxiliary elements, or respectively measuring elements 44, are not a part of the definitive tooth replacement 10. The auxiliary elements, or respectively measuring elements 44 have ends, or respectively markings 45, by means of which their angular placement can be determined. Often the two manipulation elements 42, or respectively their longitudinal axes, are neither parallel nor are they located in a common plane, instead, they take up divergent positions.

Figure 4:
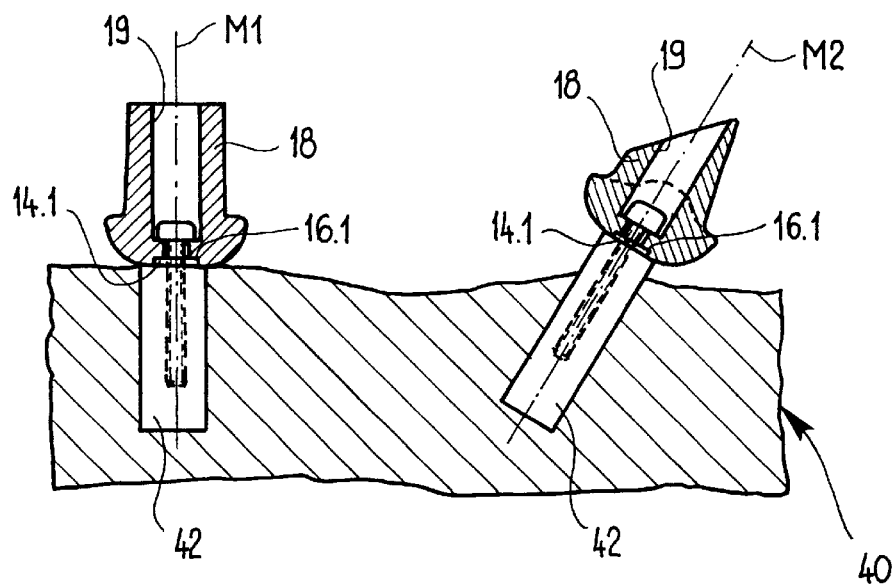
FIG. 4 shows the working model represented in FIG. 3, with abutments placed on the divergently placed implants, wherein the abutments are modified in regard to a common insertion direction, in the same view as in FIG. 3.

In a later production phase of the individual tooth replacement 10 in accordance with FIG. 4, an abutment 18 is provisionally mounted on each manipulation implant 42. On its end facing the implant, the abutment 18 has the second positioning element 16, which in the end is intended to cooperate with the complementary first positioning element 14 provided on the upper, or respectively outer, end of the implant 12 in order to constitute, together with the first positioning element 14, the positioning device 15, which is intended to prevent rotation. Correspondingly, the manipulation element 42 has a positioning element 14.1, and the auxiliary element, or respectively measuring element 44, has a positioning element 16.1, which prevent a relative rotation and secure the position.

Figure 11:
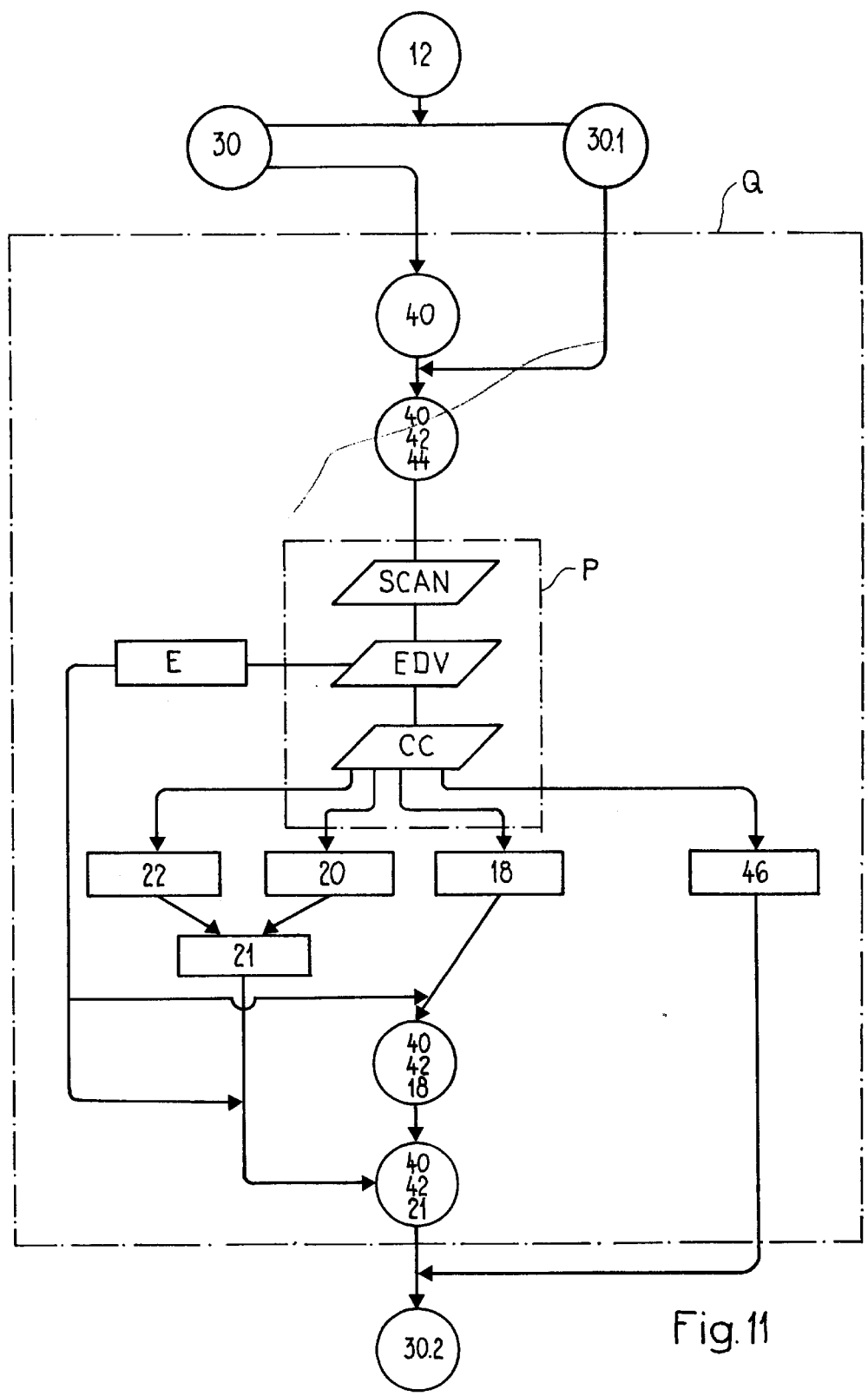
FIG. 11 is a block diagram for explaining the method in accordance with the invention for producing a tooth replacement.

The appropriate area of the working model 40, in a three-dimensional configuration, with the visible portions of the auxiliary elements, or respectively measuring element 44, but without the abutments 18, is recorded by means of a three-dimensional recording arrangement, preferably by means of a scanner SCAN, which is schematically represented in FIG. 11, and the appropriate values are memorized, or respectively stored, in a memory device of an EDP arrangement EDV. The values determined by means of the scanning operation are subsequently converted into base data BAD with the aid of the EDP arrangement EDV, which can also be integrated into a CAD arrangement, or respectively a CAM arrangement, or respectively a CAD/CAM arrangement CC. These base data BAD are used for all further calculations and automated processing operations.

Implant data ID are calculated from the base data BAD, which describe the position of the implants 12 in the jaw area 30 of the patient on the basis of the auxiliary elements, or respectively measuring elements 44, in the working model 40. It is thus possible to determine the inclination, the implant depth and the position of the implants 12 themselves, as well as the orientation of the positioning element 14, for example hex, etc., from the base data BAD, which define the position of the auxiliary elements 44.

The abutment data AD, which define the shape and intended position of the abutment, or respectively abutments, required for the respective case, can be obtained from the implant data ID, as well as from further data, which can also be obtained from a wax impression. A suitable process sequence, or respectively a suitable flow method, is selected based on these abutment data AD. Thereafter the individual abutment 18 is produced in the CAD/CAM arrangement CC by metal cutting, such as grinding and/or milling, wherein either an individual abutment blank, or a plate of abutment material, is used as the raw material, as will be described further down below. The fully automated production of the abutment 18 in the CAD/CAM arrangement CC not only assures the geometrically accurate fit, but also the keeping of the predefined material properties, since these are not subjected to unforseeable mechanical and thermal effects during the work process.

The process for making individual abutments will be covered more closely further down below.

Figure 5:
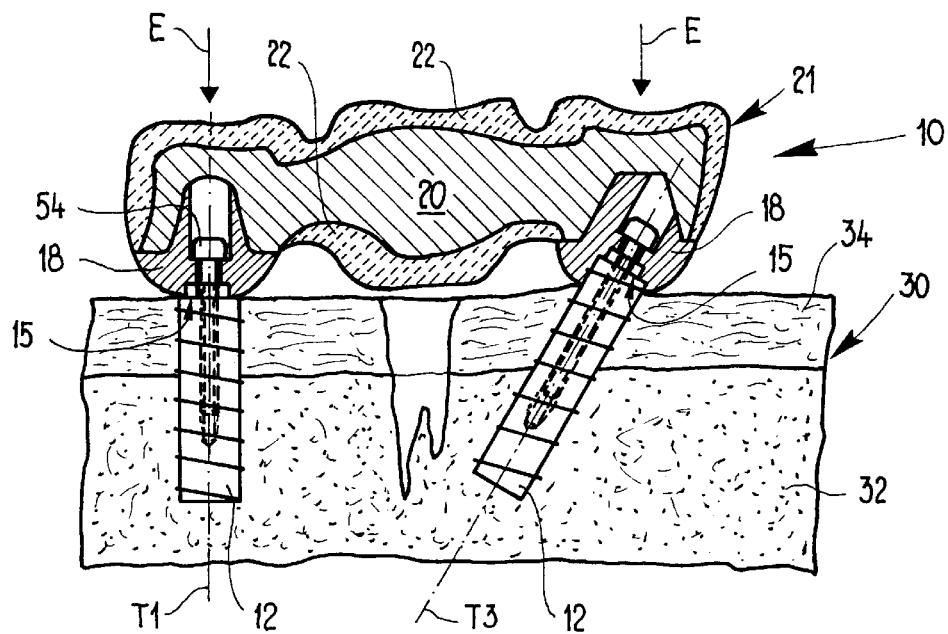
FIG. 5 shows the jaw area of the patient represented in FIG. 2 with a tooth replacement produced on the basis of the working model in FIGS. 3 and 4, in the same representation as in FIGS. 3 and 4.

If in accordance with FIGS. 2 to 6 several abutments 18 are required for the individual tooth replacement 10, which is represented in FIG. 5 in the finished state, assembled in the patient, they must be configured in such a way that the deviations in depth, orientation and angle between the implants 12 are compensated, so that afterwards the supra-structure 21, consisting of the framework 20 and the facing 22, can be mounted in a common insertion direction, without stresses being created in the implant 12, the abutments 18 and the supra-structure 21. For this purpose the EDP arrangement EDV can determine from the base data BAD not only the actual abutment data AD, but also the insertion data ED, which define the insertion direction, in particular the common insertion direction in case of several implants 12, in which the supra-structure 21 is in the end pushed on the abutments 18.

Figure 6:
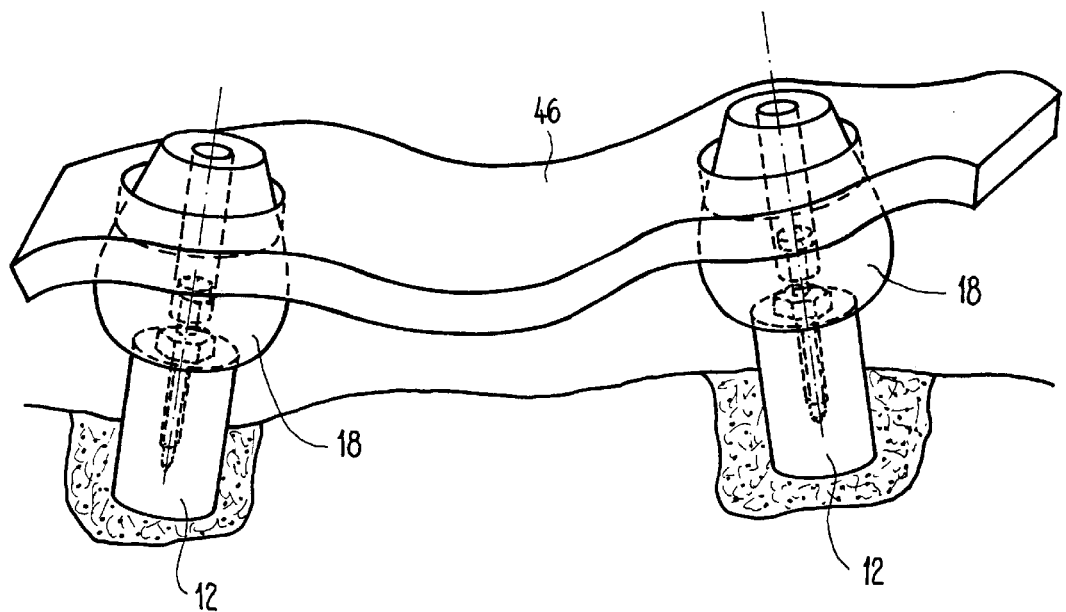
FIG. 6 shows a standard plate, represented with individual crowns and a bridge frame.

FIG. 6 shows a jaw area with two implants 12, and an abutment 18 respectively fastened thereon, as well as with a standard plate 46 for a bridge structure.

The EDP arrangement can furthermore determine framework data GD from the base data BAD, since it is essentially necessary that the inner lateral face of the framework 20 must fit on the outer, or respectively upper surface of the abutment 18, so that the facing 20 can be fastened on the abutments 18 free of stress and solidly. This does not mean that the two mentioned surfaces must be congruent, since cement is used for their fastening to each other, for which a small gap must be left open. The facing 20, or the crown- or bridge-like supra-structure 21, can also be produced with the aid of the CAD/CAM arrangement CC, in the course of which the same advantages result, which had been mentioned above in connection with the production of the abutment 18.

The individual tooth replacement 10, however without the implants, which later on support it on the jaw of the patient, is provisionally built up on the working model 40. In this case the manipulation implants 42 are used in place of the implants 12. Thereafter the transfer of the abutment 18, as well as the framework 20 and the facing 22, into the jaw area 30 of the patient takes place. This jaw area with the finished individual tooth replacement is represented in FIG. 5. In this case the abutments 18 are positioned with the aid of the positioning elements 16 on the implants 12 and fastened by means of screws. The supra-structure 21 with the framework 20 and the facing 22 is then pushed on the abutments 18, namely in the insertion direction E, which is parallel for the different abutments 18.

In the course of the production it is essential for the accuracy of the individual tooth replacement 10 that, for all purposes for which data must be employed, reference is always made to the base data BAD determined in a single scanning process, from which all further data, such as the abutment data AD, the fixation data FD, the framework data GD, the facing data VD, for example, can be directly and indirectly derived in order to use them for the shaping and processing of the various components in the CAD/CAM arrangement CC; base data BAD can also be used to produce a template, with the help of which the intended position of the inserted tooth replacement is checked. It is just as important that no manual process steps are necessary which have an effect on the precise position of the implants 12, and the position, shape and material composition of the abutment elements 18, as well as the position of the suprastructure 21. The base data BAD make possible a systematic, coherent method for constructing the individual tooth replacement.

In what follows, details of the production of the abutment 18 and abutment blanks 17 will be covered. A blank or semi-finished part is used as the abutment blank 17 for a single abutment 18, which is designed by the manufacturer to be finished and individualized in this way.

A library in the memory unit of the EDP arrangement EDV can contain the data of available pre-manufactured abutment blanks 17, which need not solely be abutment blanks 17 made of a single material or by a single manufacturer. The EDP arrangement EDV now selects the proper abutment blank 17 for each implant 12 from these available pre-manufactured abutment blanks 17. Generally the respectively suitable abutment blank 17 is one from which the suitable abutment 18 can be made with the least processing outlay. Moreover, the EDP arrangement EDV determines all geometric processing data, such as cutting and feeding speeds, for example, the amount of coolant required and other data, in accordance with which the processing unit of the CAD/CAM arrangement CC produces the abutment 18 from the abutment blank 17.

It is alternatively possible to use a manufactured standard abutment as the abutment blank 17 but, although it is offered as a finished abutment by the manufacturer and would be designed for immediate use without further processing, such a standard abutment must still be further processed and therefore individualized for producing an optimal individual tooth replacement 10.

Details regarding the production of the abutments 18 from the abutment blanks 17 are represented in FIGS. 7A and 7B. During their processing, the abutment blanks 17 are fastened on a device. In this case devices can be used which are designed for receiving a single abutment blank 17. However, it has been found to be advantageous to fasten several abutment blanks on a common device. This device in the form of a plate 50 is shown in a view from above in FIG. 7A. A maximum of eight abutment blanks 17, not represented in FIG. 7A, can be mounted on this plate 50, for example at eight locations, namely in two rows of respectively four places. The plate 50 has a positioning element 14.2 at each of the eight locations, which corresponds to the first positioning element 14 of the implant 12, or respectively the positioning element 14.1 of the manipulation implant 42, and which is designed to work together with the positioning element 16 on the abutment blank 17, or respectively on the abutment 18. Furthermore, at each of the eight locations each plate 50 contains a threaded bore 52, which is only visible in FIG. 7B. FIG. 7B represents the plate 50 in FIG. 7A in a sectional view, but with an abutment blank 17, fastened on the plate 50 by means of a screw 54, as well as with two abutment blanks 17, fastened by means of further screws 54 on the plate 50, and with an abutment 18, created from a processed abutment blank and removed from the plate 50 by releasing the screw 54. Such plates 50 are known. However, the abutments produced on them up to now had axes which were parallel in respect to the plate 50, while in actuality it is required that the various abutments have axes, which are differently oriented in respect to the plate 50. In accordance with the novel process, the directions of these axes are determined by means of the detection device SCAN by using the auxiliary elements, or respectively measuring elements 18, and are taken into consideration in the production of the abutments 18 by the CAD/CAM arrangement CC, so that the abutments 18 produced in this manner can be mounted with conforming axes.

Figure 8A:
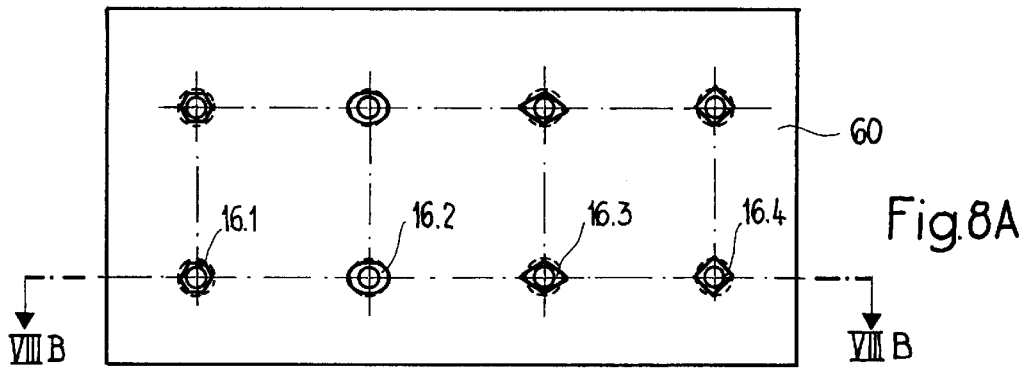
FIG. 8A is a view from above on a plate from which anatomically correct abutments can be correctly machined.
Figure 8B:
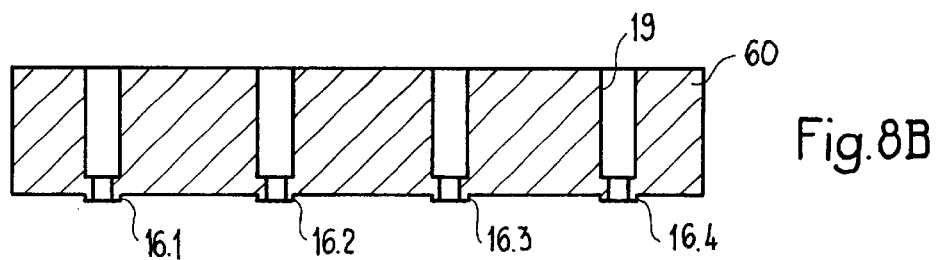
FIG. 8B shows the plate represented in FIG. 8A in a sectional view perpendicularly in respect to the main plane of the plate.
Figure 8C:
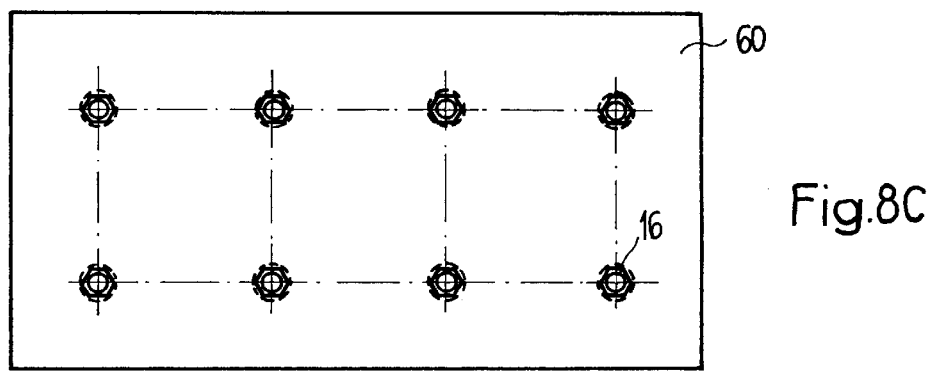
FIG. 8C represents a further plate from which abutments can be made, in the same representation as in FIG. 8A.
Figure 8D:
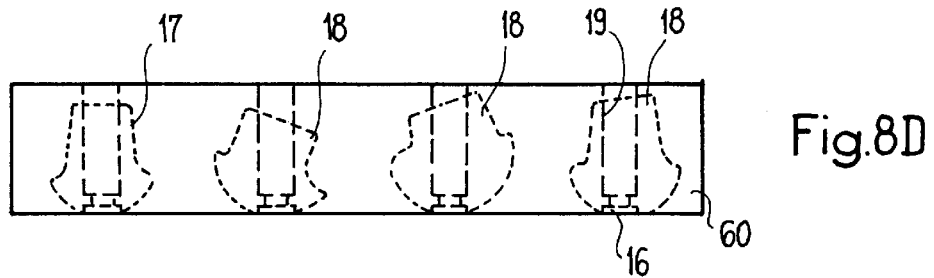
FIG. 8D is a lateral view of the plate represented in FIG. 8C, wherein the shapes of the abutments to be produced are shown in dashed lines.

A further possibility of producing abutments is represented in FIGS. 8A, 8B, 8C and 8D. In this case the abutments 18 are made directly from the plates 60. This plate 60 consists in its entirety, or at least in the areas from which the abutments 18 are created, of the material of the abutments 18 themselves, but is also used as a device for fixing the abutments 18 being created in place during their production. The plate 60 contains respectively one positioning element 16 at several locations, for example eight in the example represented, which will also constitute the positioning element 16 of the finished abutment 18. The positioning elements can have any arbitrary shape, for example a hexagon, an octagon, a rhombus, or an oval cylinder. In an example, FIG. 8A shows four variations 16.1, 16.2, 16.3, 16.4 of rotation-preventing positioning elements 16 which, in accordance with FIG. 8B, all project outward although, as represented in FIG. 8C, all positioning elements 16 of a plate 60 are generally designed in the same way. In contrast to this, the positioning elements 16 of the plate 60 in accordance with FIG. 8D are arranged in the interior of the plate 60. The plate 60 also contains the through-bores 19 and the support for a head of a screw 54, not represented here, which is later needed for fixing the finished abutments 18 in place on the implants 12. If abutments without through-bores must be produced, plates 60 without the bores 19 are to be used. Thus, eight abutments 18 can be produced from the plate 60, each one of which is designed to be fastened on an implant. The shapes of the finished abutments 18 are represented by dashed lines in FIG. 8D.

Figures 9A, 10A:
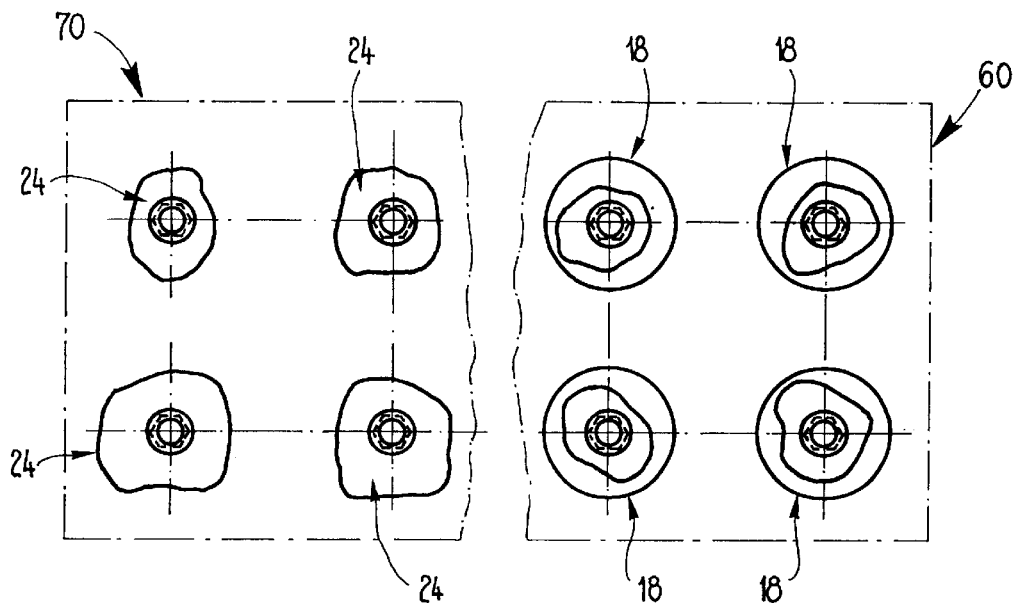
FIG. 9A shows a view from above on four abutments made from a plate in the position which they have taken up in the plate and wherein the plate is represented in dashed lines.
FIG. 10A shows four integral elements, consisting of abutments, frameworks and facings, made from a plate, in the position which they have taken up in the plate, wherein the plate is represented in dashed lines, in the same representation as in FIG. 9A.
Figures 9B, 10B:
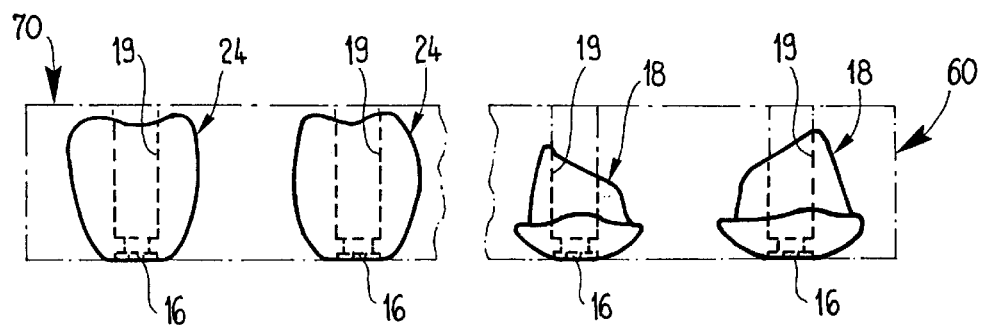
FIG. 9B is a lateral view of the abutments represented in FIG. 9A, wherein the plate from which they have been made is represented in dashed lines.
FIG. 10B shows the integral elements shows in FIG. 10A in the same representation as in FIG. 9B.

FIGS. 9A and 9B show four finished abutments 18, which were made from a plate 60.

In a representation analogous to FIGS. 9A and 9B, FIGS. 10A and 10B show how the production of an individual tooth replacement 10 can be further rationalized, in that respectively one abutment is embodied integrally with a framework, if desired also integrally with a facing, as an integral element 24 and is made in one processing operation from the same material. It is particularly advantageous to produce several integral elements 24 from one plate 70.

The abutments 18 and the integral elements 24, which are made of plates 60, or respectively 70, are separated from the plates only at the end of their being processed, if the plates 60 and 70 are directly clamped. Alternatively, during the processing of the abutments 18, or respectively the integral elements 24, the plates 60, or respectively 70, can be fastened on a device, not represented, by means of auxiliary screws, also not represented, which are received in the bore 19. By means of this the abutments 18, or respectively integral elements 24, are held until the end of their processing. Abutments, or respectively integral elements, of plates not having bores 19 can, if needed, be clamped after a first part of the processing, so that they are held to the end of processing.

It would also be possible to produce an integral element with three sections from an appropriate plate, wherein only two sections are intended for fastening on a respective implant and for this purpose have one positioning element and one through-bore each, while all three sections would be provided as a replacement for a total of three teeth, but the through-bores would have to be made at the required distance from each other for this purpose.

Up to now no attention has been paid to the question of the materials from which the implants, the abutments, the framework and the facings are made. However, this question of the materials is of decisive importance. The materials used should be as inexpensive as possible and should be workable with a reasonable effort, should have sufficient hardness, sturdiness and elasticity, and a thermal expansion value similar to the original tooth material in order not to be impaired by mechanical and thermal stresses, should be chemically resistant to all materials which are endogenic, are eaten and are used in connection with cleaning the teeth and found in the oral cavity, should be bio-compatible, and the visible areas of the tooth replacement, i.e. in particular the structural elements, should be as similar in appearance to the original teeth as possible. Moreover, it is desirable that the various components of the individual tooth replacement are made of the same material in order to avoid problems which might arise from the use of different materials, for example different thermal expansion, effects of bi-materials, such as corrosion because of the different position of adjoining materials in the electrochemical series, and an overly different service life.

Depending on the case, various materials have been shown to be particularly suitable for producing components of the individual tooth replacement. For example, suitable materials are metals, ceramic materials, glass and plastic. Therefore the processing arrangements by means of which CAM processing of abutments, for example, is performed, should be capable of processing these materials.

There are restrictions regarding the techniques which are used for producing, or respectively processing, the various components of the individual tooth replacement. In particular, molding processes and erosion processes, such as are often used conventionally, are not necessarily suitable, since stresses or changes in the material can occur because of large temperature differences. Uncontrollable changes in the materials should be avoided, in particular for medical reasons. It is also possible to use molding and erosion processes, besides other processes, without problems in connection with the mass production of blanks for implants and abutments.

When employing the method in accordance with the invention, all above mentioned requirements regarding the materials for the individual tooth replacements can be met. Less suitable molding processes in particular can be avoided, and the processing setup for performing the CAM procedure can work with all possible materials.

Figure 12:
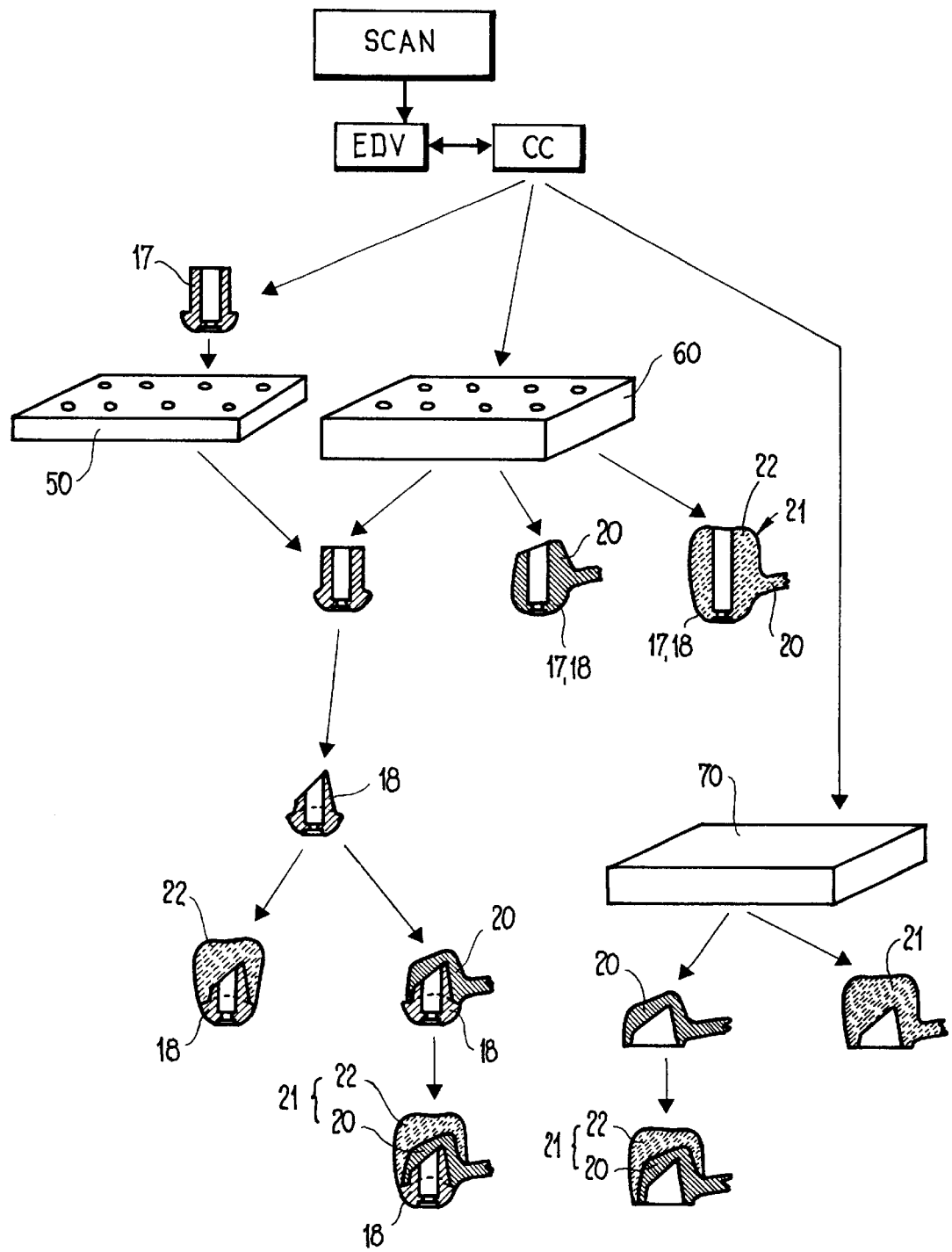
FIG. 12 is a schematic representation for explaining various production methods and production phases of tooth replacement elements.

The individual steps in an example of the entire method for producing and inserting an individual tooth replacement are made clear by means of the schematic representations in FIGS. 11 and 12.

The steps in accordance with the invention are bordered by a dash-dotted frame in FIG. 11. The working model 40, equipped with the respective components 42, 18, 20, 22 of the individual tooth replacement 10, or respectively with the auxiliary element 44, depending on the method steps taken, is always represented as a circle. The individual components used for performing the process, namely the scanner SCAN, the EDP unit EDV, as well as the CAD/CAM arrangement CC, are represented in the form of parallelograms and enclosed within a frame P, and the components 12, 16, 18, 20, 22 of the individual tooth replacement resulting from the the EDP unit EDV, and the CAD/CAM arrangement CC, as well as the auxiliary element, or respectively measuring element 44, and the data for their mounting are represented by rectangles. Components, or respectively process steps, shown outside of the frame Q, namely the jaw area 30 of the patient, which is to be provided with the individual tooth replacement 10, the negative cast 32 produced from this, the jaw area 30.1 provided with the implants 12, and the jaw area 30.2 of the patient provided with the individual tooth replacement 10, are not a part of the invention. Otherwise FIG. 11 is self-explanatory.

FIG. 12 shows the various productions variations in a clear manner, as well as the starting, intermediate and end stages of the tooth replacement, with the exception of the implant. The detection device SCAN, the EDP arrangement EDV and the CAD/CAM arrangement CC are used.

The basic material for the abutments 18 is constituted either by the abutment blanks 17, which are fastened on the plates 50 during processing, or the plates 60, which consist of abutment material. The supra-structure 21 is subsequently mounted on the abutments 18 and can consist of one element or of two elements, namely the framework 20 and the facing 22.

The plate 70 constitutes the basic material of the integral elements 24, which integrate either the abutment and the framework, or the abutment, the framework and the facing.

As mentioned above, the invention also relates to a method for producing an individual tooth replacement element, i.e. of an individual tooth replacement element made of one or several components, which can be mounted on at least one implant or at least one tooth stub. The components of the tooth replacement element are the same as the components of the above described tooth replacement, but without the implant, and therefore the tooth replacement element can basically be produced and mounted in the same way as the above described components of the tooth replacement, but of course with the exception of the implants, or respectively the manipulation implants and the specific method steps connected with them.

What is claimed is:

1. A method for designing an individually made, implant-supported tooth replacement comprising the steps of:

creating a working model of a patient's teeth and jaw;

attaching a manipulation implant to said working model corresponding to a tooth replacement position;

attaching a measuring element to said manipulation implant;

determining the three-dimensional geometry of said working model using a detection device and said measuring element;

creating base data in a computer's memory which reflects said determined three-dimensional geometry;

storing information about commercially available dental components in said computer's memory;

using said base data to automatically calculate the position, depth and inclination of an implant into the patient's jaw;

using said base data and dental component data to automatically determine the shape, starting materials and inclination of an abutment to be attached to said implant;

using said base data to automatically determine the shape and insertion direction for a framework and/or superstructure to be attached to said abutment.

2. The method of claim 1 wherein said abutment is produced from a commercially available pre-manufactured abutment blank.

3. The method of claim 1 wherein said working model is produced from a negative impression of the patient's teeth and jaw.

4. The method of claim 1 wherein said framework and/or superstructure is designed using a CAD/CAM arrangement.

5. The method of claim 1 wherein said framework and/or superstructure is produced integrally with said abutment.

6. A method for designing an individually made, implant-supported tooth replacement to replace a plurality of teeth comprising the steps of:

creating a working model of a patient's teeth and jaw;

attaching a manipulation implant to said working model at a position corresponding to each tooth to be replaced;

attaching a measuring element to each said manipulation implant;

determining the three-dimensional geometry of said working model using a detection device and said measuring elements;

creating base data in a computer's memory which reflects said determined three-dimensional geometry;

storing information about commercially available dental components in said computer's memory;

using said base data to automatically calculate the position, depth and inclination of an implant into the patient's jaw for each tooth to be replaced;

using said base data and dental component data to automatically determine the shape, starting materials and inclination of an abutment to be attached to said implant for each tooth to be replaced, wherein each abutment is fastened to its implant in an orientation which is approximately parallel to every other abutment;

using said base data to determine the shape and insertion direction for a framework and/or superstructure to be attached to said abutments so that said framework and/or superstructure can be inserted over said abutments by applying pressure in a single direction.

7. The method of claim 6 wherein said abutments are produced from commercially available pre-manufactured abutment blanks.

8. The method of claim 6 wherein said working model is produced from a negative impression of the patient's teeth and jaw.

9. The method of claim 6 wherein said framework and/or superstructure is designed using a CAD/CAM arrangement.

10. The method of claim 6 wherein said framework and/or superstructure is produced integrally with said abutment.

* * * * *